United States Patent [19]

Tomioka et al.

[11] Patent Number: 5,510,109
[45] Date of Patent: Apr. 23, 1996

[54] ANTIBACTERIAL AND ANTIFUNGAL COMPOSITION

[75] Inventors: Toshikazu Tomioka, Ibaraki; Katsumi Tomita; Mariko Tomita, both of Hirakata; Atsushi Nishino, Neyegawa, all of Japan

[73] Assignee: Matsushita Electric Industrial Co., Ltd., Osaka, Japan

[21] Appl. No.: 51,581

[22] Filed: Apr. 22, 1993

Related U.S. Application Data

[63] Continuation of Ser. No. 799,520, Nov. 27, 1991, abandoned.

[30] Foreign Application Priority Data

| | | | |
|---|---|---|---|
| Nov. 28, 1990 | [JP] | Japan | 2-332493 |
| Dec. 27, 1990 | [JP] | Japan | 2-408126 |
| May 7, 1991 | [JP] | Japan | 3-101289 |
| Jul. 19, 1991 | [JP] | Japan | 3-179315 |
| Oct. 4, 1991 | [JP] | Japan | 3-257487 |

[51] Int. Cl.$^6$ .......................... A01N 25/26; A01N 59/20
[52] U.S. Cl. .......................... 424/421; 424/404; 424/405; 424/409; 424/489; 424/76.1; 424/78.09; 424/618; 424/637; 424/641; 514/63; 514/724
[58] Field of Search .......................... 424/405, 409, 424/489, 618, 421, 711, 76.1, 76.9, 637, 641, 642, 78.09, 404

[56] References Cited

U.S. PATENT DOCUMENTS

| | | | |
|---|---|---|---|
| 1,482,906 | 7/1922 | Allen | 424/489 |
| 2,038,694 | 4/1936 | Wiggins | 167/72 |
| 3,265,571 | 8/1966 | Krezanoski | 424/711 |
| 4,107,313 | 8/1978 | Bailey | 424/263 |
| 4,169,069 | 9/1979 | Unger | 252/316 |
| 4,289,758 | 9/1981 | Van Leuven | 424/132 |

FOREIGN PATENT DOCUMENTS

| | | |
|---|---|---|
| 0103214 | 3/1984 | European Pat. Off. . |
| 0116865 | 8/1984 | European Pat. Off. . |
| 190504 | 8/1986 | European Pat. Off. . |

(List continued on next page.)

OTHER PUBLICATIONS

"Encyclopedia Chimica" (excerpt) pp. 911–912 and 1132.
H. Freiser & Q. Fernando, "Ionic Equilibria in Analytical Chemistry," pp. 145–147, 312 & 313, John Wiley & Sons, Inc. NY (1963).
JIS–Z 0701–1977 Japanese Industrial Standard Silicongel Pessicants for Packaging.
Goldstein et al. Priniciples of Drug Action 1969 pp. 16–17.
Ichikawa, Chem Abst. #114:2017582 Microbiosidal Silica gel.
Sorum *Fundamentals of Gempral Chemistry* Prentice Hall, Inc. Englewood Cliff, N.J. 1955 pp. 300–301.
Masakuni Tahara (Ed.) "Silicagel Desiccants for Packaging", *Japanese Industrial Standard* JIS Z 0701, Revised Mar. 1, 1977.
Chemical Abstract Service Abstract No. CA97(21):174528w for Y. F. Borisovich et al., "Antiviral and Toxic Properties of Silver Thiosulfate Complexes," *Tr.–Vses. Gos. Nauchno–Kontrol'n. Inst. Vet. Prep.*, 29–30 (1980) pp. 127–132.
Communication dated Apr. 2, 1992 from the European Patent Office.

*Primary Examiner*—Thurman K. Page
*Assistant Examiner*—Neil Levy
*Attorney, Agent, or Firm*—Panitch Schwarze Jacobs & Nadel

[57] ABSTRACT

An antibacterial and antifungal composition which comprises an antibacterial and antifungal material carried on a porous particle carrier is provided. Preferably, the porous particle carrier is a silica gel particle. The antibacterial and antifungal material is at least one metal complex salt, and can contain plant extracts and the like in addition to the metal complex salt. At least a portion of the surface of the above-mentioned carrier having the antibacterial and antifungal composition can be coated with a coating material.

9 Claims, 1 Drawing Sheet

FOREIGN PATENT DOCUMENTS

| | | |
|---|---|---|
| 0253663 | 1/1988 | European Pat. Off. . |
| 0270129 | 6/1988 | European Pat. Off. . |
| 0288063 | 10/1988 | European Pat. Off. . |
| 0294206 | 12/1988 | European Pat. Off. . |
| 0392262 | 10/1990 | European Pat. Off. . |
| 2364686 | 4/1978 | France . |
| 6320344 | 7/1986 | Japan . |
| 61-228283 | 11/1986 | Japan . |
| 61-268934 | 11/1986 | Japan . |
| 2292201 | 5/1989 | Japan . |
| 347101 | 6/1989 | Japan . |
| 0011275 | 4/1893 | United Kingdom ................. 424/76.7 |
| 965010 | 7/1964 | United Kingdom . |

ANTIBACTERIAL AND ANTIFUNGAL COMPOSITION

CROSS REFERENCE TO RELATED APPLICATION

This application is a continuation of application Ser. No. 07/799,520, filed Nov. 27, 1991, now abandoned.

BACKGROUND OF THE INVENTION

1. Field of the Invention

This invention relates to an antibacterial and antifungal composition, a method for the production of the composition, and an antibacterial and antifungal resin or a caulking material using the same.

2. Description of the Prior Art

As synthetic resin products have been used more frequently in recent years, contamination of the surface of synthetic resins with bacteria has become a problem when it is utilized in the field which require the care about hygiene, such as kitchen utensils. Bacteria and fungi grow on the surface of caulking materials utilized for interior materials, which cause problems in hygiene or in appearance and so on. In order to cope with these problems, an antibacterial and antifungal composition has been mixed with a synthetic resin for the purpose of exuding the composition from the resin to provide an antibacterial and antifungal properties on the surface of the resin.

To obtain a bactericidal and fungicidal effect on the surface of the resin and its surrounding by facilitating the elusion of the antibacterial and antifungal composition from the Synthetic resin, an organic antibacterial and antifungal material such as thiabendazole or the like is used. However, because of its volatility, the surrounding environment of the synthetic resin will be polluted when an organic antibacterial and antifungal material is contained in the resin. Further, waste fluid which had been contacted with the surface of the synthetic resin contains the antibacterial and antifungal material, which becomes a cause of sewage pollution and in turn influences activated sludge during effluent treatment.

Among plant extracts terpene compounds ate known to have an antibacterial effect. As techniques utilizing the terpene compounds, a therapeutic agent for Trychophyton (Japanese Laid-Open Patent Publication No. 63-30424), a refrigerator equipped with an antifungal deodorant unit comprising phytontid obtained from a plant( Japanese Laid-Open Patent Publication No. 61-228283) and an air cleaner (Japanese Laid-Open Patent Publication No. 61-368934) have been disclosed. However, since many of the substances present in the plants described above are aromatic and volatile, these substances volatilize when mixed with heated and melted resin for molding.

SUMMARY OF THE INVENTION

The antibacterial and antifungal composition of this invention, which overcomes the above-discussed and numerous other disadvantages and deficiencies of the prior art, comprises an antibacterial and antifungal material which is carried on a porous particle carrier.

In a preferred embodiment, the carrier is a silica gel particle.

In a preferred embodiment, the antibacterial and antifungal material is at least one metal complex.

In a preferred embodiment, the antibacterial and antifungal material further comprises at least one substance selected from the group consisting of plant extracts, quaternary ammonium salts, and chlorhexidine derivatives.

In a preferred embodiment, the metal complex comprises silver, copper or zinc.

In a preferred embodiment, the metal complex is a metal thiosulfato complex.

In a preferred embodiment, the metal complex is a silver thiosulfato complex.

In a preferred embodiment, the material is at least one selected from the group consisting of plant extracts, quaternary ammonium salts, and chlorhexidine derivatives.

In a preferred embodiment, the carrier is Type B silica gel particle defined in Japanese Industrial Standard JIB Z 0701.

In a preferred embodiment, the carrier is a silica gel particle with average particle size of 1–10 µm.

In a preferred embodiment, at least a portion of the surface of said silica gel particle having the antibacterial and antifungal material is coated with a coating material.

In a preferred embodiment, the coating material is at least one selected from the group consisting of reactive organic silicon compounds, wax, and stearic acid or its derivatives.

In a preferred embodiment, the porous particle carrier is a silica gel particle, the coating material is a reactive organic silicon compound, and the silica gel particle and the organic silicon compound are chemically bound.

An antibacterial and antifungal resin comprises a resin which contains the above-mentioned antibacterial and antifungal composition.

An antibacterial and antifungal caulking material comprises a base material which contains the above-mentioned antibacterial and antifungal composition.

In a preferred embodiment, the base material is a silicone gum.

In a preferred embodiment, the carrier is a zeolite particle and the antibacterial and antifungal material is a silver complex.

In a preferred embodiment, at least a part of the surface of the zeolite particle on which the silver complex is carried is coated with a coating material.

In a preferred embodiment, the carrier is a zeolite particle, the antibacterial and antifungal material is silver or a compound containing silver, and at least a part of the surface of the zeolite particle on which silver or the compound containing silver is carried is coated with a coating material.

A method for the production of an antibacterial and antifungal composition comprises the steps of:

preparing a solution of antibacterial and antifungal material; and mixing the solution and a porous particle carrier, and drying the mixture to allow the antibacterial and antifungal material to be carried on the porous particle carrier.

In a preferred embodiment, the method for the production of an antibacterial and antifungal composition further comprises the step of coating at least a portion of the surface of said carrier on which the antibacterial and antifungal material is carried is coated with a coating material.

In a preferred embodiment, the method for production of the above-mentioned antibacterial and antifungal composition of comprises the steps of:

preparing a metal thiosulfato complex solution; and mixing the metal thiosulfato complex solution and silica gel particles, and drying the mixture to allow the metal thiosulfato complex to be carried on the silica particles.

In a preferred embodiment, the step for preparing the metal thiosulfato complex comprises the process of:

adding at least one salt selected from the group consisting of sulfite and bisulfite to an aqueous solution of a metal salt; and adding a thiosulfate to the aqueous solution.

In a preferred embodiment, the step for preparing the metal thiosulfato complex comprises he process of adding a metal salt to an aqueous solution of thiosulfate.

In a preferred embodiment, the metal thiosulfate is used in an amount of 100–1000 parts by weight for every 100 parts by weight of the metal salt.

In a preferred embodiment, the metal salt is a silver salt.

In a preferred embodiment, the metal salt is a silver salt, and the thiosulfate and the silver salt are used in the ratio ranging from 2 to 6 in terms of the weight ratio of $S_2O_3^{2-}$/Ag+.

In a preferred embodiment, the metal salt is silver acetate.

In a preferred embodiment, the step for coating comprises the porous particle carrier is a silica gel particle, the coating material is a reactive organic silicon compound, and at least a portion of the surface of the silica gel particle is coated with the reactive organic silicon compound, thereby forming a chemical bonding between the organic silicon compound and the particle in the step of coating.

Thus, the invention described herein makes possible the objectives of: (1) providing an antibacterial and antifungal composition which can be contained in a resin mold, and exhibits stable antibacterial and antifungal effect on the surface of the resin mold; (2) providing an antibacterial and antifungal composition which is unlikely to become a cause of environmental pollution when it is exuded from the resin mold; (3) providing a method for the production of an antibacterial and antifungal composition having the above-mentioned excellent properties; and (4) providing an antibacterial and antifungal resin or a caulking material utilizing the antibacterial and antifungal composition having the above-mentioned excellent properties.

BRIEF DESCRIPTION OF THE DRAWING

This invention may be better understood and its numerous objects and advantages will become apparent to those skilled in the art by reference to the accompanying drawing as follows.

DESCRIPTION OF THE PREFERRED EMBODIMENTS

Figure 1:
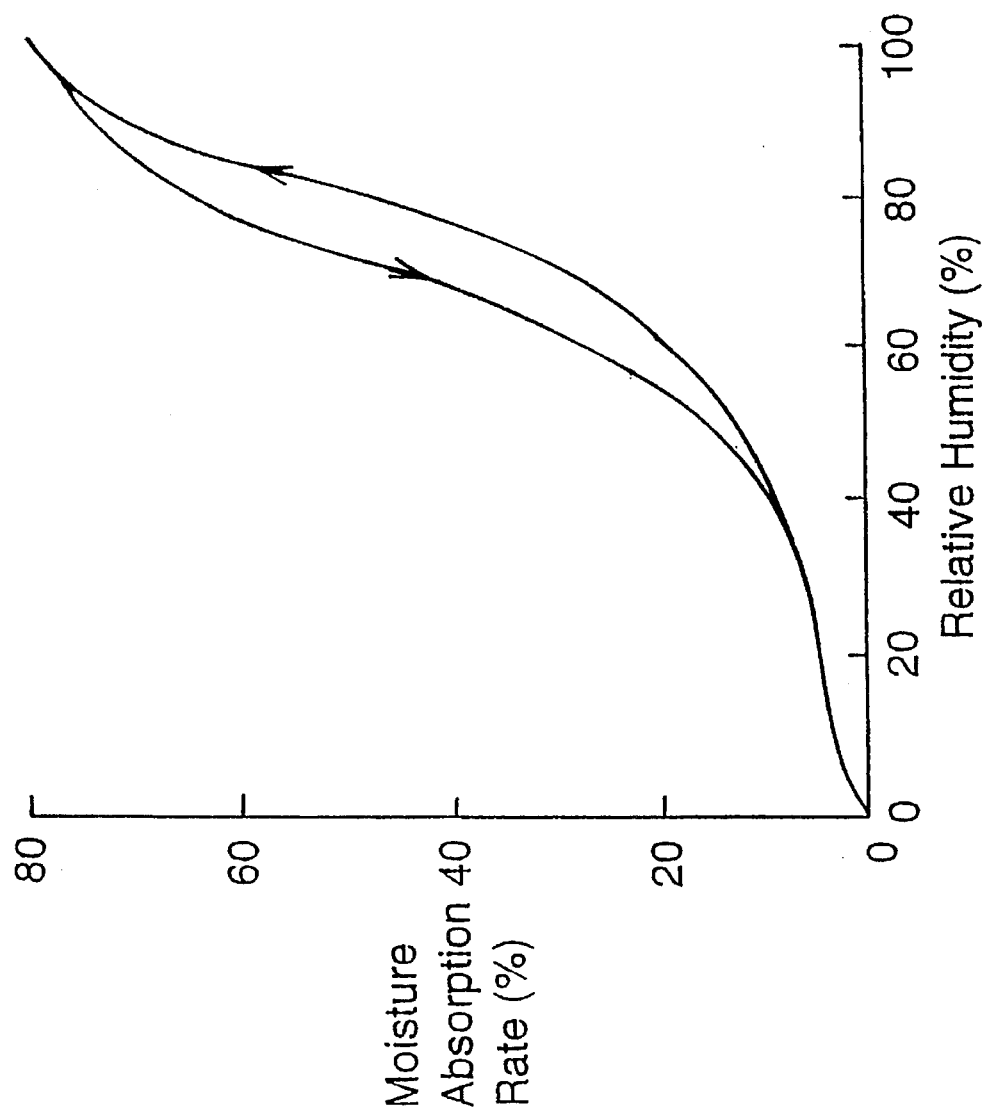
FIG. 1 illustrates the moisture absorption properties of silica gel used in one example of this invention.

For the antibacterial and antifungal material used in this invention, at least one substance selected from the group consisting of metal complexes, plant extracts, quaternary ammonium salts and chlorhexidine or its derivatives is used. Particularly, it is preferable to use one or more of the substances selected from the group consisting of plant extracts, quaternary ammonium salts and chlorhexidine or its derivatives along with one or more of the metal complexes described above. By using two or more substances selected from the above-mentioned group as an antibacterial and antifungal material, an antibacterial and antifungal composition having broader antibacterial and antifungal spectrum can be obtained. Examples of plant extracts described above include licorice extract, allylisothiocyanate, and cinnamon oil; examples of quaternary ammonium salts include a quarternary ammonium salt of silicon compound, a qua-ternary ammonium salt of aliphatic compound and benzyl-dodecyldimethylammoium chloride; and examples of cholorhexidine derivatives include chlorhexidine gluconate.

Preferable metals for metal complexes are silver, copper or zinc, but silver is more preferable. Metal thiosulfato complex is preferable for the metal complex, thus, it is more preferable to use one or more metal complexes selected from the group consisting of silver thiosulfato complex, copper thiosulfato complex and zinc thiosulfato complex, with the highest preference for silver thiosulfato complex.

As mentioned above, metal salts have been usually utilized for the antibacterial and antifungal materials. Among the metal salts, silver salt is photosensitive to light or ultraviolet rays, so that synthetic resins which contains the silver salt as an antibacterial and antifungal material changes color. In contrast, a resin which contains metal, and even silver, as an antibacterial and antifungal material of this invention i.e. stable against light or ultraviolet rays because the metal is contained as a complex. Antibacterial and antifungal materials other than the metal complexes (i.e., plant extracts, quaternary ammonium salts. etc.) are stable against light or ultraviolet rays. Thus, the antibacterial and antifungal composition of this invention is stable against light and/or ultraviolet rays. Furthermore, when an antibacterial and antifungal material i.e. metal complexes, since metal complex are not volatile, an antibacterial and antifungal composition of this invention does not cause any environmental pollution.

On the surface of the particle of the metal complex, an ozone layer is formed when particles comes into contact with oxygen in the air. Microorganisms and the like will be affected on their surface tissue when they come close to the ozone layer, thus, the metal complexes exhibit antibacterial and antifungal effect.

When the metal complex is a metal thiosulfato complex, it can be prepared using a metal salt and thiosulfate. For example, one method by which it can be prepared is where sulfite and/or bisulfite are added to an aqueous solution of a metal salt so as to react, then thiosulfate is added to form a metal thiosulfato complex. Another method is where a metal salt is added to an aqueous solution of thiosulfate to form a metal thiosulfato complex. In the former method, sulfite and/or bisulfite are used to stabilize the metal thiosulfato complex thus obtained. In the latter method, a metal thiosulfato complex can be produced without the addition of such a stabilizer.

In the preparation of a silver thiosulfato complex, it is preferable to use thiosulfate in an amount of 100–1000 parts by weight for every 100 parts by weight of a silver salt. In the case of using sulfite and/or bisulfite, it is preferable to use it in an amount of 400–2000 parts by weight for every 100 parts by weight of a silver salt.

When the metal salt is a silver salt, it is preferable that the thiosulfate and silver are used in the ratio ranging from 2 to 6 in terms of the weight ratio $S_2O_3^{2-}$/Ag+. If the ratio is less than 2, brown or black reaction products such as silver sulfate and the like are likely to be produced. On the contrary, when the ratio is greater than 6, much of unreacted thiosulfate is present. If silver thiosulfato complex containing these unreacted thiosulfate are carried on the carrier, there is a fear that the carriage of silver thiosulfato complex salt may be interfered by the carriage of these thiosulfates. By setting the ratio ranging from 2 to 6, the silver thiosulfato complex can be efficiently obtained, and the color change of the composition containing the silver thiosulfato complex can be avoided.

It is preferable to perform the step of preparation of a metal thiosulfato complex and the step of carriage of the salt to a porous particle carrier at a temperature ranging from room temperature to 60° C., for a metal thiosulfato complex readily changes to sulfide and the like by heat. This also prevents color change of the composition containing a metal thiosulfato complex.

Examples of the metal salts used for the preparation of the metal thiosulfato complex include silver acetate, silver nitrate, and the like. For increasing the stability for photoreactivity, and considering environmental safety at manufacturing and discarding, silver acetate is preferable for the metal salt.

Examples of the thiosulfate used for the preparation of the metal thiosulfato complex include sodium thiosulfate, ammonium thiosulfate, and the like. Examples of the sulfite include sodium sulfite, potassium sulfite, ammonium sulfite, potassium metasulfite, and the like. Examples of the bisulfite include sodium bisulfite, potassium bisulfite, ammonium bisulfite, and the like.

Although the porous particle carriers used in this invention include silica gel and zeolite, silica gel is preferable since it has relatively larger surface area and has much more transparency than zeolite. By utilizing silica gel particles for the carrier, antibacterial and antifungal composition that has the effect of sustained release of the antibacterial and antifungal material is preferable. It is also preferable that the average particle size of the silica gel is 1–10 μm.

Moreover, preferably, the silica gel is B type silica gel defined in Japanese Industrial Standard JIS Z 0701. This silica gel exhibits moisture absorption properties shown in FIG. 1. Among B type silica gel, the once which have 20% or lower moisture absorption rate in 50% or less relative humidity (at 25° C.) and 50% or higher moisture absorption rate in 90% or more relative humidity (at 25° C.) are particularly preferable. The moisture absorption rate mentioned above means a value obtained by dividing the moisture content by the weight of dried silica gel. The silica gel absorbs a relatively small amount of moisture in an atmosphere of low humidity and has a specifically large amount of moisture in an atmosphere of high humidity. The antibacterial and antifungal composition comprising silica gel particles on which an antibacterial and antifungal material had been carried inhibits vaporization of the antibacterial and antifungal material, and are heat stable, so that it can keep and maintain the antibacterial and antifungal properties for a long period of time. Further, the silica gel has transparency and a refractive index similar to that of synthetic resins. When the antibacterial and antifungal composition obtained by using silica gel is contained in a synthetic reisin, antibacterial and antifungal properties can be provided on the surface of the synthetic resin without coloring the synthetic resin and influencing characteristics of the synthetic resin.

In this invention, finely powdered silica gel prepared by the gaseous phase technique can also be used other than the silica gel particles described above.

To obtain the first antibacterial and antifungal composition of this invention, an aqueous or an alcohol solution of the antibacterial and antifungal material is mixed with the carrier particles, then dried promptly. This makes the antibacterial and antifungal material carried on the carrier. In this step, it is preferable to use 2–10 parts by weight of the antibacterial and antifungal material for every 100 parts by weight of the carrier. After drying, the mass of carrier particles are ground as needed.

In the second antibacterial and antifungal composition in this invention, at least a portion of the surface of the carrier on which the antibacterial and antifungal material is carried is coated with a coating material.

The coating material used in this invention is preferably at least one substance selected from the group consisting of reactive organic silicon compounds, wax and stearic acid or its derivatives; and a reactive organic silicon compound is more preferable. The reactive organic silicon compound is preferably a compound having functional groups capable of forming siloxane bonding such as tetramethoxysilane and tetraethoxysilane and the like. When the carrier is silica gel particles, and the coating material is the reactive organic silicon compound, the reactive organic silicon compound is hydrolyzed and polycondensed with the silica gel to form siloxane bonds, which results in a good coating. In this step, it is preferable to use 100–200 parts by weight of the coating material for every 100 parts by weight of the carrier on which the antibacterial and antifungal material is carried.

The antibacterial and antifungal composition becomes more heat stable by coating at least a portion of its surface with a coating material. Accordingly, in the case that the antibacterial and antifungal properties are provided on the surface of the-resin by dispersing the antibacterial and antifungal composition of the present invention in the resin, stability with respect to heat generated in the course of molding the resin can be increased, and the color of the resin can be prevented from changing over the elapse of time. Furthermore, release of the antibacterial and antifungal material is controlled, so that the antibacterial and antifungal effect will be maintained for a long period of time.

As mentioned above, it is possible to use the antibacterial and antifungal composition obtained as described above by being contained in a resin, and also, in a caulking base material. For caulking base material, room temperature vulcanizable silicone gum, two-component liquid type vulcanizable silicone, and putty caulking material can be used and room temperature vulcanizable silicone gum is preferable.

For the method for mixing an antibacterial and antifungal composition with a resin or a caulking base material, usual dispersion methods or mixing methods can be employed. It is preferable to use 1–20 parts by weight of the antibacterial and antifungal composition for every 100 parts by weight of the resin or the cauking base material.

EXAMPLES

Hereinafter, the present invention will be described by way of illustrating the examples.

Example 1

One hundred parts by weight of water soluble silver salt such as silver acetate, 450 parts by weight of the mixture of sodium sulfite and sodium bisulfite, and 300 parts by weight of water soluble thiosulfate such as sodium thiosulfate were dissolved in chlorine-free water and mixed well with stirring to obtain an aqueous solution of silver thiosulfato complex. The above-mentioned weight of the sodium thiosulfate is shown in terms of the weight of $Na_2S_2O_3 \cdot 5H_2O$.

The carrier used in this example is B type silica gel powder defined in "JIS Z 0701 silica gel desiccant for packaging". Isothermal moisture absorption properties represented as moisture absorption rate to surrounding humidity is shown in FIG. 1. The B type silica gel powder has a low moisture absorption rate in low humidity and a high moisture absorption rate in high humidity, and has an average particle size of about 8 μm.

The silica gel powder was dried at 180° C. for 2 hours or more. The aqueous solution of silver thiosulfato complex was mixed so that the amount of silver contained in the mixture is 2 parts by weight per 100 parts by weight of the silica gel powder. Next, the solvent and the moisture absorbed in the carriers were then promptly removed from the carrier. The mass of carrier particles was then ground into a given particle size to obtain silica gel particles on which the antibacterial and antifungal material was carried.

Then 100 parts by weight of the silica gel particles on which the antibacterial and antifungal material was carried were dispersed in an ethyl alcohol solution in which 100 parts by weight of tetraethoxysilane as a reactive organic silicon compound was diluted, followed by the addition of pure water to coat at least a portion of the surface of the silica gel by hydrolysis and polycondensation of tetraethoxysilane. The mixture was dried to obtain an antibacterial and antifungal composition.

Five parts by weight of the antibacterial and antifungal composition produced by the method described above was dispersed in 100 parts by weight of unsaturated polyester resin, and a mold was obtained. The resin mold was subjected to the test for antibacterial effect and the test for antifungal effects. The results are shown in Table 1.

Test for antifungal effect: The tests were performed according to the procedure of halo test by mildew proof examination for textile taken from the tests for resistance to fungus defined in Japanese Industrial Standard JIS Z 2911. The fungus used were *Cladosporium cladosporoides*, *Chaetomium globosum*, *Penicillium citrinum*, and *Asperigillus niger*. Evaluation was made after 14 days.

Test for antibacterial effect: The tests were performed according to the procedure of halo test using *Escherchia coli*, *Staphylococcus aureus*, and *Bacillus subtillis*. Evaluation was made after 7 days.

Antibacterial and antifungal materials such as plant extracts, quaternary ammonium salts, chlorhexidine digluconate and the like, can be used alternatively to silver thiosulfato complex which is used in this example. Antibacterial and antifungal materials can also be used in combination. Wax or stearic acid or its derivatives can be used as a coating material alternatively to the reactive organic silicon compound described above.

It is also possible to use silver nitrate as a water soluble silver salt for the preparation of the silver complex. It is also possible to use potassium sulfite, ammonium sulfite or the like as sulfite, and potassium bisulfite, potassium metasulfite or ammonium bisulfite or the like as bisulfite. Each of the sulfites and bisulfites can be used alone or in combination, and 400–2000 parts by weight of the sulfite and/or bisulfite is used for every 100 parts by weight of the water soluble silver salt. Ammonium thiosulfate can be used as thiosulfate with appropriate amount of 100–1000 parts by weight. Suitable average particle size for B type silica gel is 1–10 μm. Appropriate amount of silver per 100 parts by weight of silica gel powder is 2–10 parts by weight. The amount of the reactive organic silicon compound is preferably 10 to 200 parts by weight, and tetramethoxysilane can be also used instead of tetraethoxysilane.

Example 2

One hundred parts by weight of water soluble silver salt such as silver acetate, 450 parts by weight of the mixture of sodium sulfite and sodium bisulfite, and 300 parts by weight of water soluble thiosulfate such as sodium thiosulfate were dissolved in chlorine-free water and mixed well with stirring to obtain an aqueous solution of silver thiosulfato complex, the above-mentioned weight of the sodium thiosulfate is shown in terms of the weight of $Na_2S_2O_3.5H_2O$. The carrier powder used in this example is finely powdered silica gel with a particle size of about 0.05 μm which had been prepared by the gaseous phase technique. To 100 parts by weight of the finely powdered silica gel, an aqueous solution of silver thiosulfato complex was added and mixed so that the final amount of silver contained in the mixture was 2 parts by weight. Then, water in the mixture was removed promptly, and the residue was then ground into a given particle size, resulting in finely powdered silica gel on which the antibacterial and antifungal material was carried.

Then 100 parts by weight of the finely powdered silica gel on which the antibacterial and antifungal material was carried were dispersed in ethyl alcohol solution in which 100 parts by weight of tetraethoxysilane as a reactive organic silicon compound was diluted, followed by the addition of about 20 parts by weight of pure water to coat at least a portion of the surface of the finely powdered silica gel by hydrolysis and polycondensation of tetraethoxysilane. An antibacterial and antifungal material was then obtained by promptly removing the solvent and moisture absorbed in the carriers under reduced pressure at a little higher temperature than the boiling point of the solvent used. Using the antibacterial and antifungal composition obtained above, a resin mold was obtained by the same method described in Example 1. The resin mold was subjected to the test for antibacterial effect and the test for antifungal effect as described in Example 1. The results are shown in Table 1.

It is also possible to use silver nitrate as a water soluble silver salt for the preparation of the silver complex. It is also possible to use potassium sulfite, ammonium sulfite or the like as sulfite, and potassium bisulfite, potassium metasulfite or ammonium bisulfite or the like as bisulfite. Each of the sulfites and bisulfites can be used alone or in combination, and 400–2000 parts by weight of the sulfite and/or bisulfite is used for every 100 parts by weight of the water soluble silver salt. Ammonium thiosulfate can be used as a thiosulfate with an appropriate amount of 100–1000 parts by weight. The appropriate amount of silver per 100 parts by weight of finely powdered silica gel is 2–10 parts by weight. The amount of the reactive organic silicon compound is preferably 10 to 200 parts by weight, and tetramethoxysilane can be also used instead of tetraethoxysilane.

Similar results were obtained when a zeolite powder with a particle size of about 5 μm was used instead of the finely powdered silica gel prepared by the gaseous phase technique.

Example 3

One hundred parts by weight of water soluble silver salt such as silver acetate, 450 parts by weight of the mixture of sodium sulfite and sodium bisulfite, and 300 parts by weight of water soluble thiosulfate such as sodium thiosulfate were dissolved in chlorine-free water and mixed well with stirring to obtain aqueous solution of silver thiosulfato complex. The above mentioned weight of the sodium thiosulfate is shown in terms of the weight of $Na_2S_2O_3.5H_2O$.

The carrier used in this example is B type silica gel powder defined in "JIS Z 0701 silica gel desiccant for packaging". The B type silica gel powder has a low moisture absorption rate in low humidity and a high moisture absorption rate in high humidity as well as large amount of total absorbed moisture, and has an average particle size of about 3 μm.

The silica gel powder was dried at 180° C. for hours or more. The aqueous solution of silver thiosulfato complex was mixed so that the amount of silver contained in the mixture is 2 parts by weight per 100 parts by weight of the silica gel powder. Next, the solvent and the moisture absorbed in the carrier were then promptly removed from the carrier. The mass of carrier particles was then ground into a given particle size in order to obtain silica gel particles on which the antibacterial and antifungal material was carried.

Then 100 parts by weight of the silica gel particles on which the antibacterial and antifungal material was carried were dispersed in ethyl alcohol solution in which 100 parts by weight of tetraethoxysilane as a reactive organic silicon compound was diluted, followed by the addition of pure water to coat at least a portion of the surface of the silica gel by hydrolysis and polycondensation of tetraethoxysilane. The mixture was dried to obtain an antibacterial and antifungal composition. Five parts by weight of the antibacterial and antifungal composition thus obtained was dispersed homogeneously in 100 parts by weight of room temperature vulcanizable silicone gum as a caulking base material, thus obtaining an antibacterial and antifungal caulking material. The antibacterial and antifungal caulking material was subjected to the for antibacterial effect and the test for antifungal effect as described in the Example 1. The results are shown in Table 1.

Antibacterial and antifungal materials such as plant extracts, quaternary ammonium salts, chlorhexidine digluconate, and the like can be used alternatively to the silver thiosulfato complex used in this example. Antibacterial and antifungal materials can also be used in combination. Wax or stearic acid or its derivatives can be used as a coating material alternatively to the reactive organic silicon compound described above.

When two-component liquid type vulcanizable silicone caulking material or putty caulking material was used instead of room temperature vulcanizable silicone gum, similar results were obtained.

Example 4

First, 1.8 g of sodium thiosulfate was dissolved in 15 ml of pure water, and then, 200 mg silver acetate was added to the mixture, resulting in solution of silver thiosulfate complex salt. Next, 5 g of B type silica gel particles with an average particle size of 2.6 μm defined in "JIS Z 0701 silica gel desiccant for packaging", was dried at 180° C. for hours or more, then added to the solution of silver thiosulfato complex, and sufficiently dispersed. The solvent was removed, and the silica gel was vacuum dried at about 50°–60° C., ground and the silica gel particles on which the antibacterial and antifungal material has been carried were obtained.

Then 100 parts by weight of the silica gel particles on which the antibacterial and antifungal material was carried were dispersed in an ethyl alcohol solution in which 100 parts by weight of tetraethoxysilane as a reactive organic silicon compound was diluted, followed by the addition of pure water to coat at least a portion of the surface of the silica gel by hydrolysis and polycondensation of tetraethoxysilane. The mixture was dried to obtain an antibacterial and antifungal composition.

3 parts by weight of the antibacterial and antifungal composition was homogeneously dispersed in 100 parts by weight of unsaturated polyester resin to obtain a mold. The resin mold was subjected to the test for antibacterial effect and the test for antifungal effect as described in Example 1. The results are shown in Table 1.

Similar results were obtained when the other water soluble thiosulfates, such as ammonium thiosulfate, were used instead of sodium thiosulfate for preparing the silver thiosulfato complex. Similar results were also obtained when other reactive organic silicon compounds such as tetraethoxysilane were used instead of tetramethoxysilane; and when methyl alcohol was used as a solvent instead of ethyl alcohol.

Example 5

After 200 mg of silver acetate was dissolved in 30 ml of pure water at about 50°–60° C., the solution was filtered to remove undissolved residue, then 1 g of sodium sulfite and 1.8 g of sodium thiosulfate were added successively to the solution and dissolved. B type silica gel with an average particle size of about 2.6 μm defined in "JIS Z 0701 silica gel desiccant for packaging" was added to the solution, mixed and dried, resulting in silica gel particles on which an antibacterial and antifungal material was carried. The silica gel particles with the antibacterial and antifungal material were coated in the same procedure as in Example 4, resulting in an antibacterial and antifungal composition. Then, by the use of this composition, a resin mold were obtained as in Example 4. The resin mold was subjected to the test for antibacterial effect and the test for antifungal effect as described in Example 1. The results are shown in Table 1.

Example 6

The weight ratio of sodium sulfite and silver acetate used in the preparation of the silver thiosulfato complex in Example 5 was varied so that the ratio of $S_2O_3^{2-}/Ag^+$ would be a number shown In Table 2. Using the aqueous solution of the silver thiosulfato complex prepared in this way, an antibacterial and antifungal composition was obtained by the same method as in Example 4. Using this composition, a resin mold was obtained by the same method as in Example 4. The degree of color change of the resin mold was evaluated by comparing it to the standard resin mold that does not contain the composition. The results are shown in Table 2. As can be seen from Table 2, color change of the resin mold in which the ratio of $S_2O_3^{2-}/Ag^+$ is out of the range between 2 to 6 is too severe for practical use.

Similar results were obtained when other sulfites such as potassium sulfite or ammonium sulfite were used instead of sodium sulfite, and other bisulfites such as potassium bisulfite, potassium metasulfite, or ammonium bisulfite instead of sodium bisulfite were used alone, or in combination in the Examples 5 and 6 above.

Example 7

The carrier used in this example is B type silica gel powder defined in "JIS Z 0701 silica gel desiccant for packaging". Isothermal moisture absorption properties represented as moisture absorption rate to the surrounding humidity is shown in FIG. 1. Particle size of the silica gel powder is 1–3 μm and the silica gel powder was used after drying at 180° C. for two hours or more. Next, 0.02–3 parts by weight of chlorhexidine gluconate solution disclosed in Japanese pharmacopoeia was mixed in 100–300 parts by weight of a solvent such as ethyl alcohol and methyl alcohol, into which 100 parts by weight of the silica gel were dispersed and mixed. The moisture absorbed in the carrier and the solvent was then promptly removed and dried. The silica gel mass was then ground into a given particle size in order to obtain an antibacterial and antifungal composition.

In this example, a silica gel powder that has a high moisture absorption rate at a high humidity atmosphere is preferable. In contrast, the silica gel particles having a high moisture adsorption rate in an atmosphere with low humidity is not preferable, since such a silica gel particle cannot carry a large amount of antibacterial and antifungal material. A resin mold that contains the silica gel particles on which the antibacterial and antifungal material is carried does not have sufficient antibacterial and antifungal effects. Also the effects cannot be kept for a long period of time. Furthermore, water or moisture is apt to adsorb on the surface of the mold, so that the mold is hard to dry. A silica gel powder which has 20% or lower moisture absorption rate in 50% or less relative humidity (at 25° C.) and 50% or higher moisture absorption rate in 90% or more relative humidity (at 25° C.) is suitable for practical use.

Two to five parts by weight of the antibacterial and antifungal composition produced by the method described above wee dispersed in 100 parts by weight of unsaturated polyester resin in order to obtain a mold. The resin mold was subjected to the test for antibacterial effect and the test for antifungal effect by the same method as in Example 1. The results are shown in Table 1.

Example 8

An antibacterial and antifungal composition was produced in the same way as in Example 7 except that 0.05 to 5 parts by weight of benzyldodecyldimethylammoium chloride solution described in Japanese pharmacopoeia was used in place of the chlorhexidine gluconate solution and was formed into a resin mold. The resin mold was examined for antibacterial and antifungal effects in the same way as in Example 1. The results are shown in Table 1.

Example 9

An antibacterial and antifungal composition was produced in the same way as in Example 7 except that 0.1 to 10 parts by weight of quaternary ammonium salt of silicon compound, quarternary ammonium salt of aliphatic compound, or combination thereof was used in place of the chlorhexidine gluconate solution, and formed into a resin mold. The resin mold was examined for antibacterial and antifungal effects in the same way as in Example 1. The results are shown in Table 1.

Example 10

An antibacterial and antifungal composition was produced in the same way as in Example 7 except that 0.05 to 5 parts by weight of licorice extract described in Japanese pharmacopoeia was used in place of the chlorhexidine gluconate solution and formed into a resin mold. The resin mold was examined for antibacterial and antifungal effects in the same way as in Example 1. The results are shown in Table 1.

Example 11

An antibacterial and antifungal composition was produced in the same way as in Example 7 except that 0.2 to 10 parts by weight of cinnamon oil described in Japanese pharmacopoeia was used in place of the chlorhexidine gluconate solution and formed into a resin mold. The resin mold was examined for antibacterial and antifungal effects in the same way as in Example 1. The results are shown in Table 1.

Example 12

First, 0.001, 0.01, 0.1, 1.0, 5.0 and 10.0 g of allylisothiocyanate were respectively mixed with 10 g of alcohol. To this mixture, 10 g of silica gel powder was added and mixed. The moisture absorption rate of the silica gel used was about 80% and the average particle size was about 8 μm. The mixture was then put into an oven adjusted to 100° C., and alcohol was evaporated to dryness and ground into a particle size of 10 μm or less. The composition so obtained was mixed with 500 g of polypropylene resin, polyethylene resin or unsaturated polyester. When the polypropylene resin or the polyethylene resin was used, a master batch was prepared by mixing the above composition with a resin powder, after which this matter batch was fused by heating it together with the same kind of resin to form a mold. When the unsaturated polyester was used, the total amount of resin and the above composition were mixed to be molded. The resulting resin mold was examined for antibacterial and antifungal effects in the same way as in Example 1. In this case, the evaluation of the antibacterial test was conducted 24 hours later. The results are shown in Table 3.

From the results in Table 3, it was noted that the practical antibacterial effect was obtained by mixing the composition containing allylisothiocyanate in an amount of 0.1 to 80 parts by weight based on 100 parts by weight of the silica gel powder with 5,000 parts by weight of the unsaturated polyester; and the practical antifungal effect was obtained by mixing the composition containing allylisothiocyanate in an amount of 50 to 80 parts by weight based on 100 parts by weight of the above silica gel powder with 5,000 parts by weight of the unsaturated polyester. When the amount of silica gel on which allylisothiocyanate wee carried was 10 parts by weight or more with respect to 100 parts by weight of the resin, the appearance of the resin mold was extremely damaged. Similar results were obtained when the polyethylene resin was used.

Example 13

First, 50 parts by weight of silica gel particles on which the antibacterial and antifungal material obtained in Example 1 was carried and which was coated with tetraethoxysilane was mixed with 50 parts by weight of silica gel particles on which the antibacterial and antifungal material obtained in Example 7 was carried. Then, a resin mold was obtained by using this mixture in the same way as in Example 1. The resulting resin mold was examined for antibacterial and antifungal effects in the same way as in Example 1. The results are shown in Table 1.

Example 14

First, 100 parts by weight of silica gel particles on which the antibacterial and the antifungal material obtained in Example 1 was carried and which was coated with tetraethoxysilane was dispersed to be mixed into a solution in which 100 to 500 parts by weight of licorice extract described in Japanese pharmacopoeia, was mixed with 100 to 500 parts by weight of solvent such as ethyl alcohol or methyl alcohol. Then, the mixture was dried by removing the solvent and moisture absorbed in the carrier at a temperature slightly higher than the boiling point of the solvent. The dried mixture was ground into a given particle size, thereby obtaining silica gel particles onto which two kinds of antibacterial and antifungal materials were carried. A resin mold was obtained by using this silica gel powder in the same way as in Example 1. The resulting resin mold was examined for antibacterial and antifungal effects in the same way as in Example 1. The results are shown in Table 1.

Example 15

A resin mold was obtained in the same way as in Example 1 without coating the silica gel particles, on which the antibacterial and antifungal composition of Example 1 was carried, with tetraethoxysilane. When the polyester resin was used, the mold so obtained was reacted with a hardening agent, thus obtaining a colored mold. The resulting resin mold was examined for antibacterial and antifungal effects in the same way as in Example 1. The results are shown in Table 1.

Comparative Example 1

A resin composition was obtained in the same way as in Example 1, except that only unsaturated polyester resin was molded and hardened without using the antibacterial and antifungal composition. The resulting resin mold was examined for antibacterial and antifungal effects in the same way as in Example 1. The results are shown in Table 1.

Comparative Example 2

A resin composition was obtained in the same way as in Example 3 except that only a caulking base material for room temperature vulcanizable silicone gum was molded without using antibacterial and antifungal composition. The resulting resin mold was examined for antibacterial and antifungal effects in the same way as in Example 1. The results are shown in Table 1.

TABLE 1

| | Mixture of four kinds of fungi | E. Coli | S. aureus | B. subtillis |
|---|---|---|---|---|
| Example 1 | + | + | + | ± |
| Example 2 | + | + | + | ± |
| Example 3 | + | + | + | ± |
| Example 4 | + | + | + | ± |
| Example 5 | + | + | + | ± |
| Example 7 | ++ | ++ | ++ | ++ |
| Example 8 | ++ | ++ | ++ | ++ |
| Example 9 | ++ | ++ | ++ | ++ |
| Example 10 | + | ++ | ++ | + |

TABLE 1-continued

| | Mixture of four kinds of fungi | E. Coli | S. aureus | B. subtillis |
|---|---|---|---|---|
| Example 11 | + | ++ | + | ± |
| Example 13 | ++ | ++ | ++ | ++ |
| Example 14 | ++ | ++ | ++ | ++ |
| Example 15 | ++ | ++ | ++ | ++ |
| Comparative Example 1 | − | − | − | − |
| Comparative Example 2 | − | − | − | − |

++: Diameter of halo is 10 mm or larger.
+: Diameter of halo is 2 mm or larger.
±: Diameter of halo is 0 mm.
−: Bacteria or fungi grows on resin.

TABLE 2

| $S_2O_3^{2-}/Ag^+$ | Color change after mixing of resin |
|---|---|
| 1 | Color changed |
| 2 | No change |
| 3 | No change |
| 4 | No change |
| 5 | Slightly changed |
| 6 | Slightly changed |
| 7 | Color changed |

TABLE 3

| Amount of added allyl isocyanate(g) | Amount of carried allyl isocyanate(g) | Mixture of four kinds of fungi | E. coli | S. areus | B. subtillis |
|---|---|---|---|---|---|
| 0.001 | 0.001 | − | − | − | − |
| 0.01 | 0.01 | − | + | − | − |
| 0.1 | 0.1 | − | ++ | + | − |
| 1.0 | 1.0 | − | ++ | + | − |
| 5.0 | 5.0 | + | ++ | + | − |
| 10.0 | 8.0 | ++ | ++ | ++ | − |

++: Diameter of halo is 10 mm or larger.
+: Diameter of halo is 2 mm or larger.
±: Diameter of halo is 0 mm.
−: Bacteria or fungi grows on resin.

It is understood from Table 1 that the antibacterial and antifungal compositions in the present examples have practical antibacterial and antifungal efficiency.

It is understood that various other modifications will be apparent to and can be readily made by those skilled in the art without departing from the scope and spirit of this invention. Accordingly, it is not intended that the scope of the claims appended hereto be limited to description as set forth herein, but rather that the claims be construed as encompassing all the features of patentable novelty that reside In the present invention, including all features that would be treated as equivalents thereof by those skilled in the art to which this invention pertains.

What is claimed is:

1. An antibacterial and antifungal composition comprising a bactericidally and fungicidally effective amount of an antibacterial and antifungal material which is carried on a silica gel particle, wherein said antibacterial and antifungal material is at least one metal thiosulfato complex which is obtained by adding at least one compound selected from the group consisting of sulfite and bisulfite to an aqueous solution of a metal salt so as to react, followed by the addition of thiosulfate, or by adding a metal salt to an aqueous solution of thiosulfate, wherein said metal thiosulfato complex is one selected from the group consisting of silver thiosulfato complex, copper thiosulfato complex and zinc thiosulfato complex, p1 wherein said silica gel particle has an average particle size of 1–10 μm.

2. An antibacterial and antifungal resin comprising the antibacterial and antifungal composition of claim 1.

3. An antibacterial and antifungal composition of claim 1, wherein said antibacterial and antifungal material further comprises at least one substance selected from the group consisting of plant extracts, quaternary ammonium salts, and chlorhexidines and salts thereof.

4. An antibacterial and antifungal composition of claim 1, wherein said metal thiosulfato complex is a silver thiosulfato complex.

5. An antibacterial and antifungal composition of claim 1, wherein said silica gel particle has 20% or lower moisture absorption rate in 50% or less relative humidity at 25° C. and 50% or higher moisture absorption rate in 90% or more relative humidity at 25° C.

6. An antibacterial and antifungal composition of claim 1, wherein at least a portion of the surface of said silica gel particle having the antibacterial and antifungal material is coated with a coating material.

7. An antibacterial and antifungal composition of claim 6, wherein said coating material is at least one selected from the group consisting of reactive organic silicon compounds, wax, and stearic acid or its derivatives.

8. An antibacterial and antifungal composition of claim 7, wherein said coating material is a reactive organic silicon compound, and said silica gel particle and the organic silicon compound are chemically bound.

9. An antibacterial and antifungal resin comprising an antibacterial and antifungal composition of claim 6.

* * * * *

UNITED STATES PATENT AND TRADEMARK OFFICE
CERTIFICATE OF CORRECTION

PATENT NO. : 5,510,109

DATED : April 23, 1996

INVENTOR(S) : Toshikazu Tomioka et al.

It is certified that error appears in the above-indentified patent and that said Letters Patent is hereby corrected as shown below:

```
     Column 1, line 34, delete "Synthetic" and insert
--synthetic--; line 43, delete "ate" and insert --are--; and
line 50, delete "61-368934" and insert --61-268934--.
     Column 2, line 15, delete "JIB" and insert --JIS--.
     Column 3, line 11, delete "metal".
     Column 4, line 18, delete "i.e." and insert --is--; line
25, delete "i.e." and insert --is a--; line 25, delete
"complexes" and insert --complex--; line 26, delete "complex"
and insert
--complexes--; and line 63, delete "salt".
     Column 5, line 32, delete "once" and insert --ones--.
     Column 6, line 24, delete "the-resin" and insert
  --the resin--.
```

UNITED STATES PATENT AND TRADEMARK OFFICE
CERTIFICATE OF CORRECTION

PATENT NO. : 5,510,109
DATED : April 23, 1996
INVENTOR(S) : Toshihikazu Tomioka et al It is certified that error appears in the above-indentified patent and that said Letters Patent is hereby corrected as shown below:

```
    Column 8, line 4, delete "," and insert --.--; line 5,
delete "the" and insert --The--.
    Column 9, line 5, insert --2-- before "hours"; line 29
insert --test-- before the first occurrence of "for"; line 50
delete "salt"; and line 52 insert "two" before "hours".
    Column 10, line 39, delete "In" and insert--in--.
    Column 11, line 25, delete "wee" and insert --was--.
    Column 12, line 21, delete "matter" and insert --master--;
line 39, delete "wee" and insert --was--.
    Column 14, line 60, delete "In" and insert --in--.
    Column 15, line 11, delete "p1".
```

Signed and Sealed this

Twenty-second Day of July, 1997

*Attest:*

*Attesting Officer*

BRUCE LEHMAN

*Commissioner of Patents and Trademarks*